US007983460B2

(12) United States Patent
Licato et al.

(10) Patent No.: US 7,983,460 B2
(45) Date of Patent: Jul. 19, 2011

(54) METHOD AND SYSTEM FOR PERFORMING HIGH TEMPORAL RESOLUTION BOLUS DETECTION USING CT IMAGE PROJECTION DATA

(75) Inventors: Paul E. Licato, Wauwatosa, WI (US); Bernice E. Hoppel, Delafield, WI (US)

(73) Assignee: General Electric Company, Schenectady, NY (US)

( * ) Notice: Subject to any disclaimer, the term of this patent is extended or adjusted under 35 U.S.C. 154(b) by 1075 days.

(21) Appl. No.: 11/811,210

(22) Filed: Jun. 8, 2007

(65) Prior Publication Data

US 2008/0304728 A1  Dec. 11, 2008

(51) Int. Cl.
*G06K 9/00* (2006.01)
*G01N 23/04* (2006.01)

(52) U.S. Cl. .......................... 382/128; 382/274; 378/62

(58) Field of Classification Search .................. 382/128, 382/129, 130, 131, 132, 133, 134, 154, 162, 382/165, 168, 169, 181, 189, 219–224, 232, 382/254, 274, 276, 291, 305, 312; 600/410, 600/420, 425; 378/62
See application file for complete search history.

(56) References Cited

U.S. PATENT DOCUMENTS

| 6,574,304 | B1 * | 6/2003 | Hsieh et al. ...................... 378/62 |
| 6,708,055 | B2 * | 3/2004 | Geiser et al. ................... 600/425 |
| 7,020,314 | B1 * | 3/2006 | Suri et al. ...................... 382/130 |
| 7,069,068 | B1 * | 6/2006 | Ostergaard ..................... 600/420 |
| 7,343,193 | B2 * | 3/2008 | Block et al. ................... 600/410 |
| 7,738,683 | B2 * | 6/2010 | Cahill et al. .................. 382/128 |

FOREIGN PATENT DOCUMENTS

| EP | 1171028 B1 | 11/2005 |
| WO | WO 9836683 * | 2/1997 |
| WO | 9836683 | 8/1998 |
| WO | 2005094686 A2 | 10/2005 |

* cited by examiner

*Primary Examiner* — Seyed Azarian

(74) *Attorney, Agent, or Firm* — Dean Small; The Small Patent Law Group

(57) ABSTRACT

A method of evaluating changes in contrast of an image using a diagnostic imaging system is provided. The method provides acquiring raw image data of an organ or tissue, calculating a baseline of data based on the raw image data acquired before arrival of an agent, and determining changes in a signal intensity of the agent based on changes in the raw image data compared to the baseline. The agent may be an imaging agent, a contrast agent, a biomedical agent, a needle, a catheter, a biomedical device, and the like.

20 Claims, 5 Drawing Sheets

METHOD AND SYSTEM FOR PERFORMING HIGH TEMPORAL RESOLUTION BOLUS DETECTION USING CT IMAGE PROJECTION DATA

BACKGROUND OF THE INVENTION

The invention relates generally to methods and apparatus for computed tomography (CT) imaging, and more particularly to methods and apparatus for updating rendered images using CT image projection data.

In certain known CT imaging systems, an x-ray source transmits x-ray beams towards an object of interest. The x-ray beams pass through the object being imaged, such as a patient. The beams, after being attenuated by the object, impinge upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. Attenuation measurements from the detectors are acquired separately for each detector element and collectively define a projection data set or transmission profile.

The x-ray source and the detector array are rotated on a gantry within an imaging plane around the object to be imaged such that the angle at which the x-ray beam intersects the object constantly changes. A group of x-ray attenuation measurements, e.g., projection data set, from the detector array at one gantry angle is referred to as a "view." A "scan" of the object comprises a set of views made at different gantry angles, or view angles, during one revolution of the x-ray source and detector. The projection data sets are processed to construct images that correspond to two-dimensional slices taken through the object at various angles. One exemplary method for forming an image from a projection data set is referred to as filtered back projection technique.

Conventional CT medical imaging systems that acquire images without using a contrast agent result in poor visualization of the blood vessels of interest. Previous image-based methods utilized an entire set of views to be processed to generate an image. The use of an intravenous (IV) contrast medium enhances the images and allows a patient's anatomy (e.g., vessels) to be displayed more clearly. Using current medical imaging systems, it is often difficult to determine when the contrast medium arrives at an area of interest. Therefore, the imaging system may be turned on, and scanning of the area of interest may begin before the contrast medium arrives. At times, a non-contrast scan may be taken to establish a baseline image for the area to be monitored before delivery of the contrast medium. The baseline image may be then used to align the patient and the region of interest within the imaging device. By starting the imaging system in advance of the arrival of the contrast medium, the patient may be exposed to unnecessary radiation for a period of time. For instance, in an arterial study, the patient may be exposed to about 15 seconds of additional radiation before the contrast medium arrives at the region of interest. Furthermore, the longer the scanning period, the more intravenous contrast is administered to the patient, which increases costs and increases the risk of extravasation.

It is desirable to provide a CT system that shortens the scan times, reduces the total amount of IV contrast administered, and improves patient safety. It is also desirable to provide a CT system that can detect and monitor the flow of the contrast through region of interest with higher temporal resolution, such that early detection of the contrast in a region of interest is provided and the flow velocity of the contrast through the vein may be measured.

BRIEF SUMMARY OF THE INVENTION

In one embodiment, a method of evaluating changes in contrast of an image using a diagnostic imaging system is provided. The method includes acquiring raw image data of an organ or tissue, calculating a baseline of data based on the raw image data acquired before arrival of an agent, and determining changes in a signal intensity of the agent based on changes in the raw image data compared to the baseline. The agent may be an imaging agent, a contrast agent, a biomedical agent, a needle, a catheter, a biomedical device, and the like.

In another embodiment, a computed tomographic (CT) imaging system for reconstructing an image of an object is provided. The system includes an x-ray source, a detector array, a gantry, and a computer. The gantry is coupled to the x-ray source and the detector array. The gantry is configured to rotate within a scan plane around the object. The computer is coupled to the detector array and the x-ray, and the computer is configured to obtain projection data for each view of a gantry angle for an object, where the projection data for each view of the gantry angle defines a projection data set. The computer then reconstructs an image of the object using one of the individual projection data sets.

In yet, an alternative embodiment, a computer readable medium encoded with a program code segment executable by a computer for reconstructing an image of an object is provided. The computer readable segment is programmed to instruct the computer to obtain projection data for each of a plurality of views of a region of interest, where the projection data for each view of a gantry angle defines a projection data set. The segment further instructs the computer to reconstruct an image of the region of interest using one of the individual projection data sets.

DETAILED DESCRIPTION OF THE INVENTION

Figure 1:
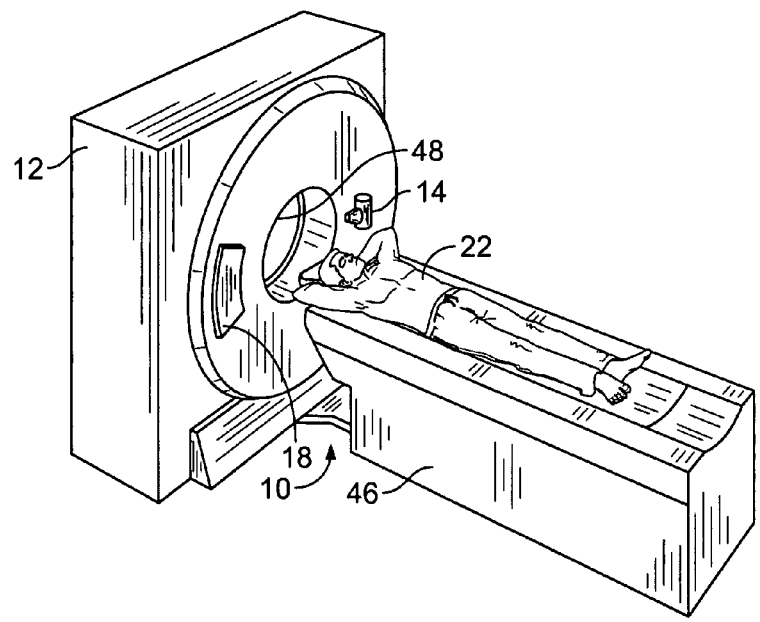
FIG. 1 illustrates a CT imaging system constructed in accordance with an embodiment of the present invention.

In the following detailed description, reference is made to the accompanying drawings which form a part hereof, and in which is shown by way of illustration specific embodiments in which the present invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

In this document, the terms "a" or "an" are used, to include one or more than one. In this document, the term "or" is used to refer to a nonexclusive or, unless otherwise indicated. In addition, as used herein, the phrase "pixel" also includes embodiments of the present invention where the data is represented by a "voxel". Thus, both the terms "pixel" and "voxel" may be used interchangeably throughout this document.

Also as used herein, the phrase "reconstructing an image" is not intended to exclude embodiments of the present invention in which data representing an image is generated, but a viewable image is not. Therefore, as used herein, the term "image" broadly refers to both viewable images and data representing a viewable image. However, many embodiments generate (or are configured to generate) at least one viewable image.

Various embodiments may be implemented in connection with different types of imaging systems. For example, various embodiments may be implemented in connection with a CT imaging system in which an x-ray source projects a fan-shaped beam that is collimated to lie within an X-Y plane of a Cartesian coordinate system and generally referred to as an "imaging plane." The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurement from all the detectors is acquired separately to produce a transmission profile.

In third generation CT systems, the x-ray source and the detector array are rotated with a gantry within the imaging plane and around the object to be imaged such that the angle at which the x-ray beam intersects the object constantly changes. A complete gantry rotation occurs when the gantry concludes one full 360 degree revolution. A group of x-ray attenuation measurements (e.g., projection data), from the detector array at one gantry angle is referred to as a "view." A view is, therefore, each incremental position of the gantry. A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as a filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for a prescribed number of slices is acquired, thereby provided a "cork screw" pattern of acquisition. Such a system generates a single helix from a fan beam helical scan. The helix mapped out by the fan beam yields projection data form which images in each prescribed slice may be reconstructed. Alternatively, an "axial" scan (e.g., a single rotation without the table moving) may be performed. Optionally, a "cine" scan (e.g., as the gantry spins during multiple cycles at the same location as multiple images are acquired during each turn of the gantry) may be performed.

Reconstruction algorithms for helical scanning typically use helical weighting algorithms that weight the acquired data as a function of view angle and detector channel index. Specifically, prior to a filtered backprojection process, the data is weighted according to a helical weighing factor, which is a function of both the gantry angle and the detector angle. The weighted data is then processed to generate CT numbers and to construct an image that corresponds to a two-dimensional slice taken through the object.

To further reduce the total acquisition time, multi-slice CT may be used. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

Figure 2:
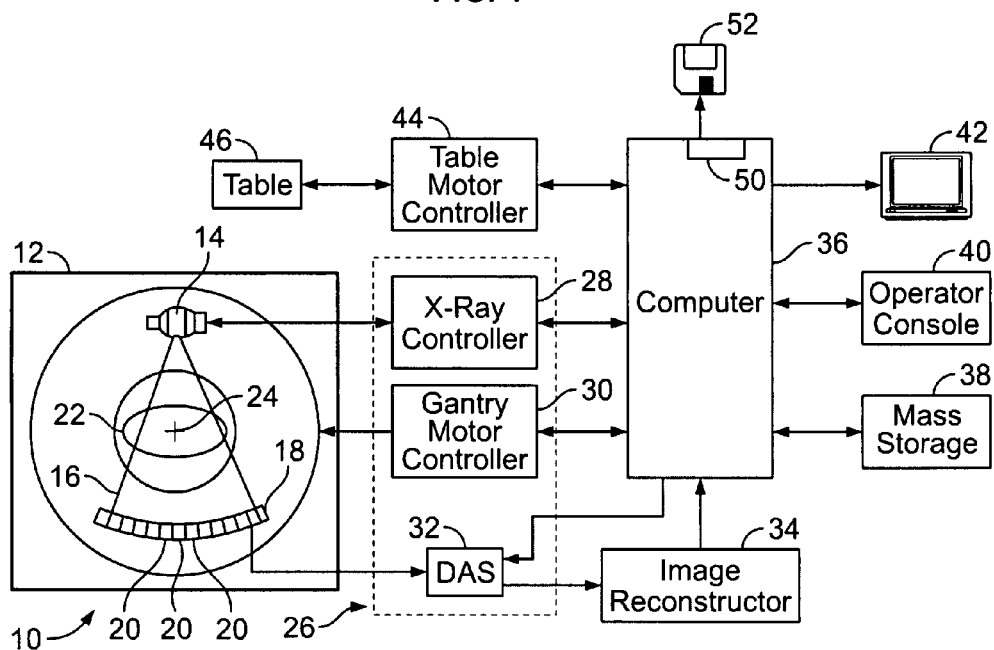
FIG. 2 illustrates a block diagram of the system illustrated in FIG. 1.

Referring to FIGS. 1 and 2, a computed tomography (CT) imaging system 10 is shown that includes a gantry 12 for a CT scanner. Gantry 12 has a radiation source such as an x-ray source 14 that projects a beam of radiation such as x-rays 16 toward a detector array 18 on the opposite side of gantry 12. Detector array 18 is formed by a plurality of detector rows (not shown) including a plurality of detector elements 20 that together sense the projected x-rays that pass through an object 22, for example a medical patient, between array 18 and source 14. Detector array 18 may be fabricated in a single slice or multi-slice configuration. Each detector element 20 produces an electrical signal that represents the intensity of an impinging radiation (e.g., x-ray) beam and hence can be used to estimate the attenuation of the beam as the beam passes through object or patient 22. During a scan to acquire x-ray projection data, gantry 12 and the components mounted thereon rotate about a center of rotation 24. FIG. 2 shows only a single row of detector elements 20 (e.g., a detector row). However, multi-slice detector array 18 may include a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. The DAS 32 outputs projection data sets including attenuation measurements obtained at particular gantry rotation angles (e.g., view angles). As the gantry 12 rotates a plurality of views may be acquired during a single rotation. A single rotation being one complete 360 degree revolution of the gantry 12. Each view has a corresponding view angle and thus, a particular location on the gantry 12. At least one-thousand views may be acquired in one gantry 12 rotation (e.g., each view angle being about 0.36 degrees). As discussed below each view may be assigned a corresponding view angle. However, a view may occupy a range of view angles (e.g., 132.3 degrees to 135.7 degrees). Alternatively, a set of views (e.g., a subset) may be acquired where each view may be separated by an interval. The interval may be selected by a user or pre-programmed into the system and may be fixed or variable. Furthermore, a subset of views may be selected such that each view is randomly selected and the interval is not consistent.

The projection data sets correspond to a particular view angle as the gantry 12 rotates about a patient 22. A group of projection data sets form a complete scan of the patient 22. For instance, a complete scan of a region of interest of the patient 22 may include a complete set of projection data sets (e.g., multiple projection data sets corresponding to multiple views during a single complete rotation of gantry 12). An image reconstructor 34 receives sampled and digitized x-ray data from DAS 32 and performs high-speed image reconstruction. The reconstructor 34 may produce data sets that represent volumetric data sets or image slices through patient 22. The reconstructed image is output by the image reconstructor 34 and applied as an input to a computer 36, which stores the image in a storage device 38 (e.g., memory). The image reconstructor 34 can be specialized hardware or computer programs executing on computer 36.

Computer 36 also receives commands and scanning parameters from an operator via console 40 that has a keyboard. An associated cathode ray tube display 42 or other suitable display device allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). In some configurations, computer 36 and/or image reconstructor 34 is/are programmed to perform functions described herein. Also, as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (e.g., a stationary detector with a rotating x-ray source) and fifth generation CT systems (e.g., a stationary detector and an x-ray source). Additionally, it is contemplated that the benefits of the invention accrue to imaging modalities other than CT, for example, MRI, SPECT, and PET.

Thus, each projection data set is associated with a particular table position and gantry rotation angle at which the projection data set was acquired. Each corresponding projection data set is stored in memory 38. The memory 38 stores a group of projection data sets for a complete scan or examination of patient 22, a group of projection data sets that correspond to a volumetric area of the patient 22, as well as projection data sets used to update an image, and optionally, subsets thereof.

Figure 3:
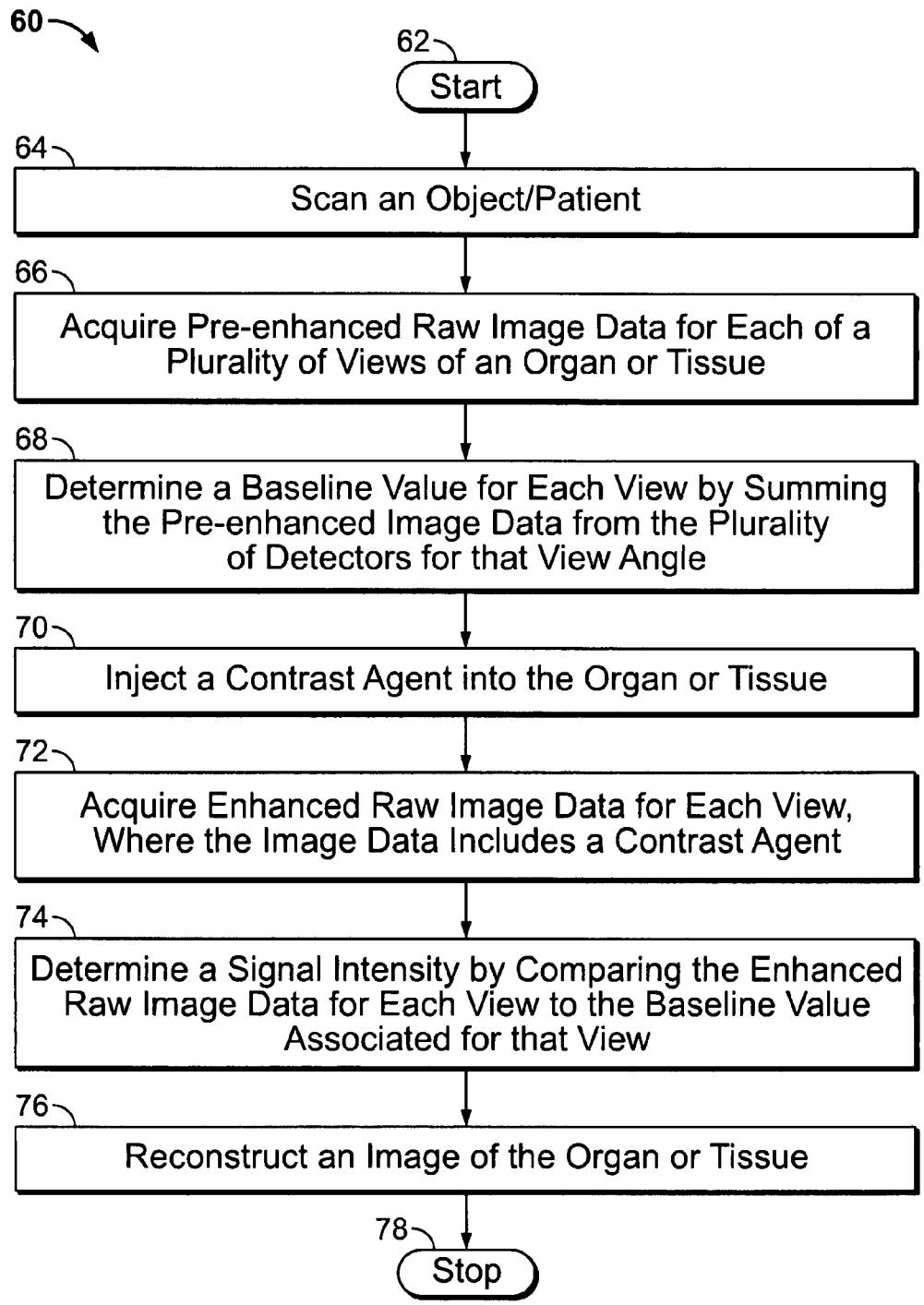
FIG. 3 is a flowchart of a process for reconstructing an image formed in accordance with an embodiment of the present invention.

FIG. 3 illustrates a process 60 for detecting a bolus of an intravenous contrast agent (or a medical device such as a needle or a catheter) by reconstructing an image formed in accordance with an embodiment of the present invention. At 62, the process commences by initiating the diagnostic imaging system to cause the gantry 12 to start revolving around a patient 22. At 64, as the gantry 12 rotates, the system may scan the patient. In one embodiment the initial scan (e.g., first complete rotation scan) may be a low dose scan (e.g., a percentage lower than a full power scan).

At 66, pre-enhanced raw image data for a plurality of views, for example, of the organ or tissue are acquired. The raw image data in one embodiment of the invention is a volumetric data set. For instance, the raw image data may be least one of a three-dimensional single cardiac phase data set, a three-dimensional multiple cardiac phase data set, a three-dimensional multi-temporal phase data set, projection data, paired projection data, conjugate projection data, calibrated raw data, sinogram data, and the like.

At 68 a baseline value for each view angle is determined for each view angle by summing the pre-enhanced image data from the plurality of detectors for that particular view angle. The pre-enhancement image data does not contain an imaging enhancing agent nor a medical device, such as a needle or catheter. For instance, for each pre-enhancement gantry rotation (e.g., before a contrast agent is injected into an organ or tissue), each view is summed over all of the selected detector rows, resulting in a single scalar value for each view, $V_{i,t}$, where $0 \leq i \leq$ Number of Views and t=0, T, 2T, ..., NT, where T is the sample period for each image. The resulting baseline scalar values are stored in memory 38 as a set of angle-dependent or view-dependent baseline views. Therefore, for each view, a scalar is assigned to a baseline view designated as $B_i = V_{i,0}$. Thus, a set of baseline views may be created before the arrival of the contrast agent.

At 70, as scanning continues a bolus of intravenous contrast agent may be injected into the patient. The contrast agent may be an imaging enhancing agent, a biomedical agent, a blood agent, a nonionic contrast agent, an iodinated contrast agent, a gadolinium-based contrast agent, an ionic contrast agent, a barium contrast agent, a barium sulfate contrast agent, an imaging agent, and an iothalamate meglumine contrast agent, among others. Alternatively, instead of a bolus of a contrast agent, a needle or a catheter, or another type of medical/biomedical device may be inserted into the organ/tissue/body part.

At 72, enhanced raw image data may be acquired for each view, where the raw image data includes a contrast agent. The scan may be a SmartPrep or timing bolus scan as provided by GE Healthcare, Milwaukee, Wis. Alternatively, the image data may contain information regarding a needle, catheter or any other type of medical device inserted into the body part. As the gantry 12 rotates, a new set of view scalars may be acquired as the contrast agent moves into the tissue (organ or body part of interest), through the tissue, and out of the tissue.

As the gantry 12 rotates, a plurality of enhanced views may be acquired during a single rotation (e.g., 1000 views may be taken in one single gantry 12 rotation). Alternatively, a set of enhanced views (e.g., a subset) may be acquired, where each view may be separated by an interval. For example, a subset of enhanced views may be acquired, where every even view is selected. Alternatively, a subset of enhanced views may include every fifth view, tenth view, twentieth view, as well as other combinations of views. Furthermore, a subset of enhanced views may be selected such that each enhanced view is randomly selected and the interval is not consistent between each view. Furthermore, a subset of enhanced views may include multiple views from multiple rotations of gantry 12. The interval may be selected by a user or pre-programmed into the system. The interval may be an interval of time or the interval may be a position of the gantry 12 (e.g., determined by the number of degrees of separation between angle views).

Figure 4:
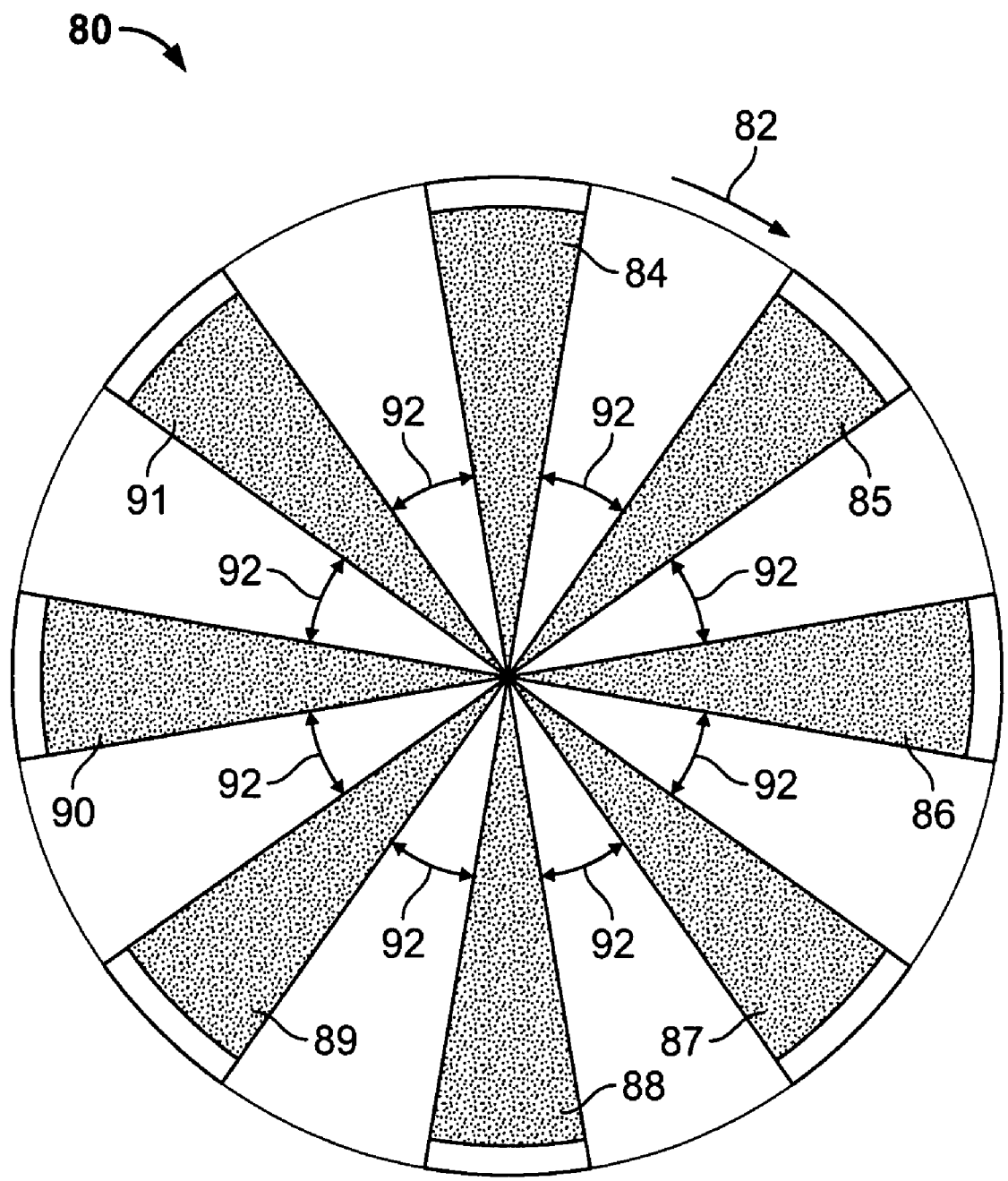
FIG. 4 is a schematic illustration of a plurality of views acquired during a single gantry rotation in accordance with an embodiment of the present invention.

For example, FIG. 4 shows a plurality of enhanced views acquired during a single gantry rotation in accordance with an embodiment of the present invention. A plurality of enhanced views may be acquired during a single rotation of gantry 12 as the contrast agent moves through the body of the patient to an organ or tissue. A plurality of enhanced views 84-91 of the patient 22 are obtained, as the gantry 12 rotates, for example, in a clockwise direction as indicated by the arrow 82. In this exemplary embodiment, each enhanced view is separated by a predetermined interval 92 (e.g., sixty degrees; however the interval could be any interval value or no interval). The user may select to use all eight enhanced views 84-91. Alternatively, the user may select to use one enhanced view 84, or a combination of the enhanced views 84-91. The projection data for each view may be stored in memory 38.

Returning to FIG. 3, at 74, a signal intensity is determined for each view. For instance, each view scalar is subtracted from a corresponding baseline value, (e.g., $V_i=V_i-B_i$). The resulting view scalar represents a signal variation over the baseline. As an example, with the arrival of the contrast bolus, the value of the signal intensity V will increase in magnitude, reach a peak at the peak arterial phase, and then diminish as the contrast bolus washes out. Changes to the signal intensity are based on changes in the raw image data. The raw image data may be analyzed using at least a statistical measurement (e.g., a mode, a mean, a weighted mean, a median, a z-score, a standard deviation, a maximum, a minimum, a range, an interquartile range, a mean difference, a midrange mean, an average absolute deviation, a student t-test, p-values, and the like), a shape of the agent, a flux of the agent, and attenuation of the x-rays caused by the agent to determine changes to the signal intensity as the contrast flows. The raw image data may also be analyzed by a noise pattern produced by the contrast agent. For example, typically there are more counts in a data set that has less noise; however, the more attenuation caused by the contrast agent, the more noise is produced. By using statistical methods to fit the noise, changes in the signal intensity may be determined. Thus, changes in the signal intensity are determined by statistical changes that produce a higher temporal resolution of the data set compared to a full image reconstruction. Flow or perfusion properties of the contrast agent may be determined based on a statistical measurement, a shape of the contrast agent flowing through the organ or tissue (e.g., the shape of the output of the dynamic agent may fit a sigmoidal curve or a exponential curve), an attenuation of the contrast agent within the organ or tissue, a flux of the contrast agent, a partial obstruction of the contrast agent, a blockage of the contrast agent by a body part, a partial obstruction of the contrast agent, and a blockage of the contrast agent. The changes in signal intensity are displayed as a function of time, as shown in FIG. 6.

Figure 6:
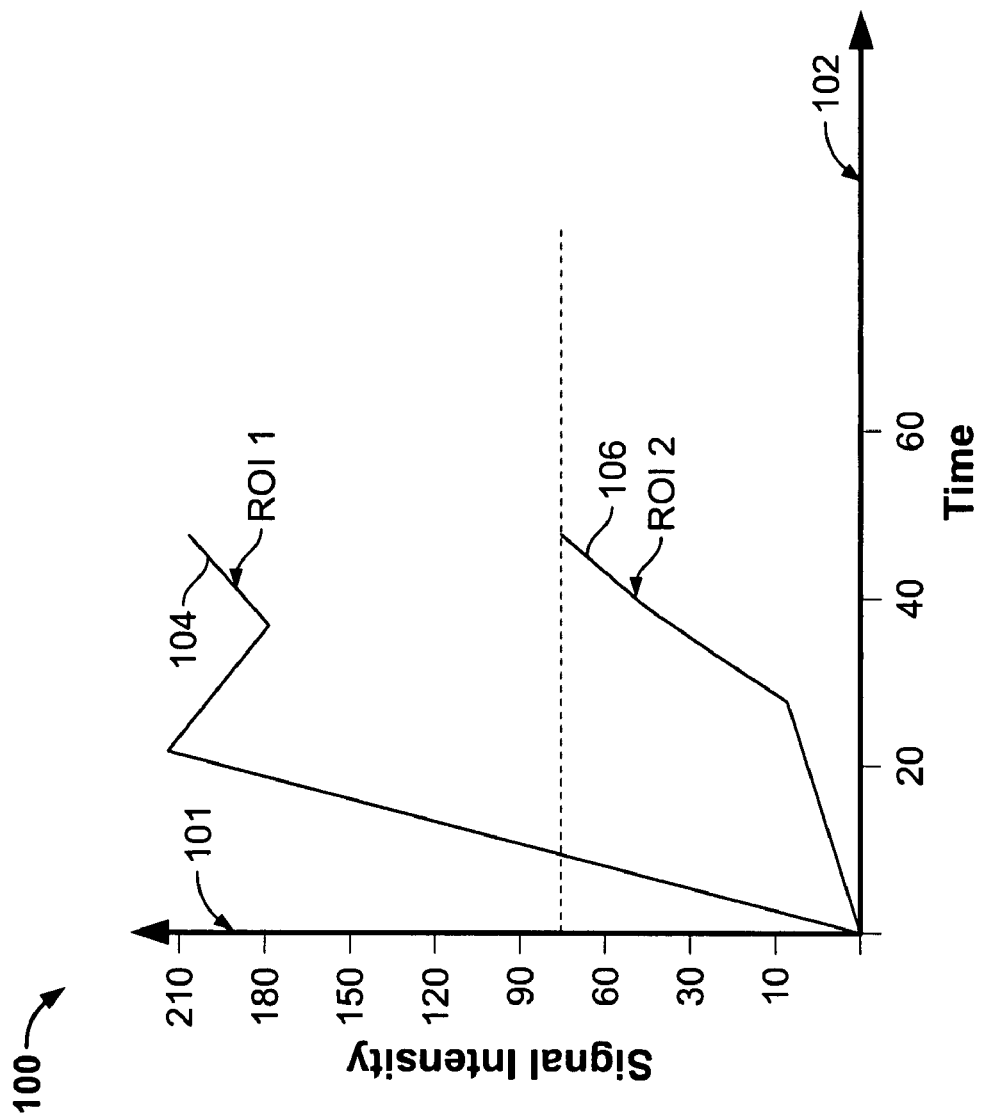
FIG. 6 illustrates a plot of a signal intensity utilized in accordance with an embodiment of the present invention.

FIG. 6 illustrates a plot 100 of signal intensity used in connection with determining the flow of a bolus of contrast over a period of time. The plot 100 identifieson the vertical axis 101, the value of signal intensity or attenuation caused by the bolus, and on the horizontal axis 102, the time the bolus takes to travel through an organ or tissue. Specifically, plot 100 depicts two regions of interest, ROI1 104 and ROI2 106. ROI1 104 shows initially a large signal intensity that drops and then rises again, whereas ROI2 106 shows a gradual increasing signal intensity.

Thus, processing the raw image data may be used to determine a clearance of the agent throughout the organ, a whole organ uptake of the agent, a regional uptake of the agent, a regional washout of the agent, a regional accumulation of the agent, a regional persistence of the agent, a regional clearance of the agent, a whole organ washout of the agent, a clearance of the agent in the tissue over the plurality of phases, and a distribution of the agent in the tissue.

Figure 5:
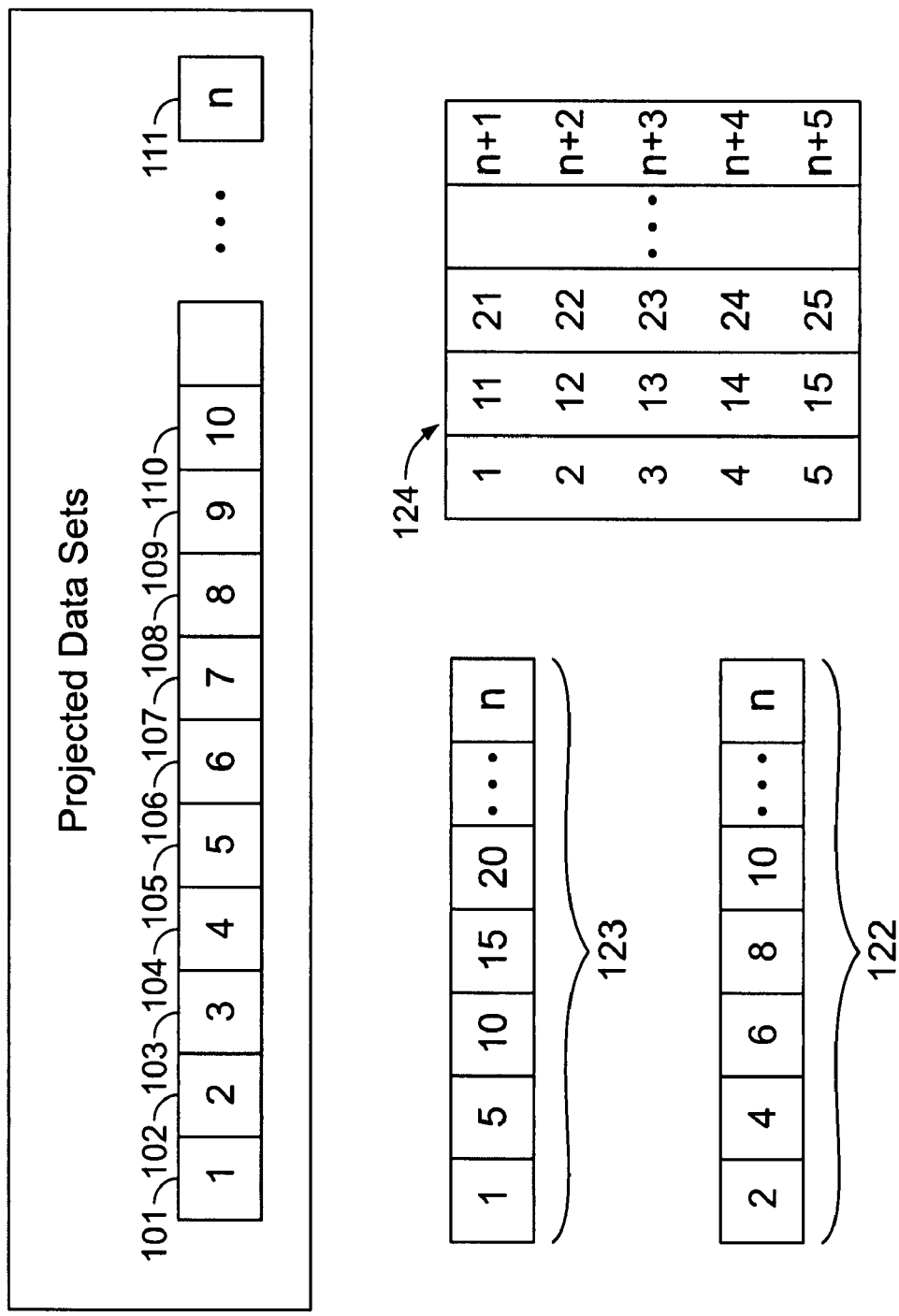
FIG. 5 illustrates a sequence of projection data sets utilized in accordance with an embodiment of the present invention.

Returning to FIG. 3, at 76, an image of the region of interest may be reconstructed or updated using one or more of the individual projection data sets (e.g. various subsets). Further, when reconstructing the image, the user may select which views to combine. When combining the views at this step, each view has been subtracted from the respective baseline view to provide a new view. Thus, each view corresponds to a particular projected data set. For example, as shown in FIG. 5, the image may be reconstructed with projection data from a single view (e.g., projection data set 1), or from multiple views where every other projection data set is selected (e.g., projection data set 122 composed of projection data sets 2, 4, 6, 8, 10 . . . n), or every fifth projection data set is selected (e.g., projection data set 123 that includes projection data sets 1, 5, 10, 15, 20, . . . n). Alternatively, the image may be reconstructed from groups of projection data sets (e.g., group 124 that includes projection data sets 1, 2, 3, 4, 5, 11, 12, 13, 14, 15, 21, 22, 23, 24, 25, . . . n+1, n+2, n+3, n+5, n+5). Thus, the user may select to combine the projection data sets in any combination of his/her choice based on the type of examination, type of scan, patient characteristics, and the like Furthermore, as additional projection data sets are used to reconstruct the image, the image resolution may be increased. For instance, each projection data set based on a view angle may be used to update the reconstructed image in real-time. The image may be updated by using a single view and the corresponding projection data set. Alternatively, the image may be updated using a subset of views. Updating the image may include some but not all the views acquired during a complete rotation of gantry 12. By using a single projection data set from one view angle, the image may be updated in real-time before the gantry 12 completes a complete rotation. Furthermore, updating the image in real-time may be possible by continuously combining projection data from multiple view angles. For example, combining multiple projection data sets may provide an image of the incremental movement of a bolus of contrast agent moving toward or into a region of interest or a medical device, such as a needle or a catheter, moving into a region of interest. Based on the dynamic changes in the projection data, a bolus transit time and a bolus flow velocity may be determined using statistical parameters, a shape of the agent, a flux of the agent, the attenuation caused by the agent, and a noise pattern produced by the agent as described above. Therefore, the image may be updated in real-time. At 78, the process 60 may be terminated or repeated again by the user.

A technical effect of the various embodiments is to use a diagnostic imaging system, such as a computed tomography (CT) imaging system to provide an improved image of an intravenous contrast agent or a medical device entering a region of interest. Furthermore, as the contrast agent moves through the patients body, dynamic changes to the contrast agent itself may be monitored, such as a shape of the contrast agent flowing through the region of interest, x-ray attenuation created by the contrast agent as the contrast agent flows into and through the region of interest, the flux of the contrast agent as the agent moves, and/or the effects of a partial or total obstruction of the contrast agent. Similarly, as a medical device, such as a catheter or needle are inserted into a region of interest, the system provides the ability to monitor the movement of the medical device into the region of interest in real time, by updating an image using projection data acquired from a single view.

The various embodiments or components thereof may be implemented as part of a computer system. The computer system may include a computer, an input device, a display unit, and an interface, for example, for accessing the Internet. The microprocessor may be connected to a communication bus. The computer may also include a memory. The memory may include Random Access Memory (RAM) and Read Only Memory (ROM). The computer system further may include a storage device, which may be a hard disk drive or a removable storage drive such as a floppy disk drive, optical disk drive, and the like. The storage device can also be other similar means for loading computer programs or other instructions into the computer system.

In various embodiments of the invention, the method of creating a CT attenuation correction image as described herein or any of its components may be embodied in the form of a processing machine. Typical examples of a processing machine include a general-purpose computer, a programmed microprocessor, a digital signal processor (DSP), a microcontroller, a peripheral integrated circuit element, and other devices or arrangements of devices, which are capable of implementing the steps that constitute the methods described herein.

As used herein, the term "computer" may include any processor-based or microprocessor-based system including systems using microcontrollers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer".

The processing machine executes a set of instructions (e.g., corresponding to the method steps described herein) that are stored in one or more storage elements (also referred to as computer usable medium). The storage element may be in the form of a database or a physical memory element present in the processing machine. The storage elements may also hold data or other information as desired or needed. The physical memory can be, for example, but not limited to, an electronic, magnetic, optical, electromagnetic, infrared, or semiconductor system, apparatus, device, or propagation medium. More specific examples of the physical memory include, but are not limited to, the following: a random access memory (RAM) a read-only memory (ROM), an erasable programmable read-only memory (EPROM or Flash memory), a Hard Disc Drive (HDD) and a compact disc read-only memory (CDROM). The above memory types are exemplary only, and are thus limiting as to the types of memory usable for storage of a computer program.

The set of instructions may include various commands that instruct the processing machine to perform specific operations such as the processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

In various embodiments of the invention, the method of creating an ultrasound medical image can be implemented in software, hardware, or a combination thereof. The methods provided by various embodiments of the present invention, for example, can be implemented in software by using standard programming languages such as, for example, C, C++, Java, and the like. As used herein, the terms "software" and "firmware" are interchangeable, and include any computer program stored in memory for execution by a computer.

Additionally, although the herein described methods are described in a medical setting, it is contemplated that the benefits also accrue to PET and CT systems. The analysis described above may be performed on several different data sets. The analyzed data set may be modified to focus on the motion of specific organs or structures. The physiological structure may include a biological organ, for example, the brain, stomach, heart, lung or liver; a biological structure, for example, the diaphragm, chest wall, rib cage, rib, spine, sternum or pelvis; or a foreign object fiducial marker, for example, a marker placed for the purpose of gating; a tumor, or a lesion or sore, for example, a bone compression fracture.

Thus, what is provided is a method and system for detecting a bolus of an intravenous contrast agent using a diagnostic imaging system, such as CT. The method and system provide the capability to obtain projection data for each of a plurality of views of a region of interest, wherein the projection data for each view of a gantry angle defines a projection data set, and to reconstruct an image of the region of interest using one of the individual projection data sets. The method and system also provide the ability to measure the uptake of the contrast agent using projection data from a selected set of view angles, wherein the selected set views are less than the number of views defining a complete gantry rotation. Furthermore, the method and system provide the ability to monitor the insertion of a medical device, such as a catheter or needle, into a region of interest using projection data sets from a selected set of views, as views are updated in real-time.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A method of determining changes in contrast of an image using a diagnostic imaging system, comprising:

acquiring raw image data of at least one of an organ or tissue, wherein the raw image data includes at least a volumetric data set;

calculating a baseline for the volumetric data set based on the raw image data acquired before arrival of an agent; and determining changes in a signal intensity of the agent based on changes in the raw image data compared to the baseline.

2. The method according to claim 1, wherein the raw image data comprises at least one of a three-dimensional single cardiac phase data set, a three-dimensional multiple cardiac phase data set, a three-dimensional multi-temporal phase data set, projection data, paired projection data, conjugate projection data, calibrated raw data, and sinogram data.

3. The method according to claim 1, wherein changes to the signal intensity are based on changes in the raw data based on at least one of a statistical measurement, a shape of the agent, a noise pattern produced by the agent, a flux of the agent, and attenuation of x-rays caused by the agent.

4. The method according to claim 1, wherein the agent comprises at least one of an imaging agent, a contrast agent, a biomedical agent, a needle, a catheter and a biomedical device.

5. The method according to claim 1, further comprising determining at least one of a flow and a perfusion property of the agent based on at least one of a statistical measurement, a shape of the contrast agent flowing through the organ or tissue, an attenuation of the contrast agent within the organ or tissue, a flux of the contrast agent, a partial obstruction of the contrast agent, and a blockage of the contrast agent by a body part, a partial obstruction of the contrast agent, and a blockage of the contrast agent, wherein the agent is at least one of a contrast agent, an imaging agent and a biomedical agent.

6. The method according to claim 1, further comprising processing the raw image data to determine at least one of a clearance of the agent throughout the organ, a whole organ uptake of the agent, a regional uptake of the agent, a regional washout of the agent, a regional accumulation of the agent, a regional persistence of the agent, a regional clearance of the agent, a whole organ washout of the agent, a clearance of the agent in the tissue over the plurality of phases, a distribution of the agent in the tissue, wherein the agent is at least one of a contrast agent, an imaging agent and a biomedical agent.

7. The method according to claim 1, wherein changes in the signal intensity are determined by statistical changes that produce a higher temporal resolution of the data set.

8. The method according to claim 1, wherein changes in the signal intensity are determined by statistical changes that are displayed as a function of time.

9. The method according to claim 2, wherein the signal intensity is updated in real-time for a range of projection angles.

10. The method according to claim 2, further comprising comparing an enhanced image to a baseline image to determine dynamic changes in the projection data, wherein the enhanced image is based on the acquired views of at least one of the organ and the tissue that includes an imaging enhancing agent and the baseline image is based on acquired views of at least one of the organ and the tissue that do not include an imaging enhancing agent.

11. The method according to claim 10, further comprising determining at least one of a bolus transit time and a bolus flow velocity based on dynamic changes in projection data.

12. The method according to claim 2, further comprising updating the image based on projection data from at least a single view.

13. A computed tomographic (CT) imaging system for reconstructing an image of an object, said imaging system comprising:

an x-ray source;

a detector array;

a gantry coupled to the x-ray source and the detector array, the gantry configured to rotate within a scan plane around the object;

a computer coupled to the detector array and the x-ray, the computer configured to:

obtain projection data for each of a plurality of views of a gantry angle for an object, wherein the projection data for each view of the gantry angle defines a projection data set; and reconstruct an image of the object using one or more of the projection data sets for a subset of the plurality of views that is less than a total number of views defining a complete gantry revolution; and updating the image based on the subset of the plurality of views.

14. The system in accordance with claim 13, wherein the image is updated in real-time using multiple projection data sets, each projection data set is acquired from a different view angle, wherein the selected views are less than the number of views defining a complete gantry revolution.

15. The system in accordance with claim 13, wherein the computer is further configured to determine the uptake of a contrast agent into the object by using by projection data from a selected set of view angles, wherein the selected set of views are less than the number of views defining a complete gantry rotation.

16. The system in accordance with claim 13, wherein the computer is further configured to monitor the insertion of a medical device into the object by computing a signal intensity of the region of interest for the projection data from each selected view, wherein the views are updated in real-time.

17. The system in accordance with claim 13, wherein reconstructing an image comprises updating the image using selected projection data sets from more than one revolution of the gantry.

18. The system in accordance with claim 13, wherein reconstructing an image comprises updating the image from a selected set of views, each view spaced at intervals around the gantry.

19. The system in accordance with claim 13, wherein reconstructing an image comprises updating the image based on projection data acquired in less than one revolution of the gantry.

20. A computer readable medium encoded with a program code segment executable by a computer for reconstructing an image of an object, said segment programmed to instruct the computer to:

obtain projection data for each of a plurality of views of a region of interest, wherein the projection data for each view of a gantry angle defines a projection data set; and reconstruct an image of the object using one or more than one of the individual projection data sets for a subset of the plurality of views that is less than a total number of views defining a complete gantry revolution; and updating the image based on the subset of the plurality of views.

* * * * *